(12) United States Patent
Claypool et al.

(10) Patent No.: US 6,371,580 B1
(45) Date of Patent: Apr. 16, 2002

(54) CONSOLE FOR GLASS FORMING MACHINE

(75) Inventors: Mark P. Claypool, Horseheads; Thomas M. Beiswenger, Corning, both of NY (US); Peter Wirz, Meggen; Janusz Konaszewski, Winterthur, both of (CH)

(73) Assignee: Emhart Glass S.A. (CH)

( * ) Notice: Subject to any disclaimer, the term of this patent is extended or adjusted under 35 U.S.C. 154(b) by 0 days.

(21) Appl. No.: 09/694,470

(22) Filed: Oct. 23, 2000

(51) Int. Cl.[7] ............................................. A47B 53/00
(52) U.S. Cl. .................. 312/120; 312/7.2; 312/138.1; 348/839
(58) Field of Search .............................. 312/7.2, 138.1, 312/120, 117, 327, 328, 249.7; 348/836, 839

(56) References Cited

U.S. PATENT DOCUMENTS 1,638,813 A * 8/1927 Cochran .................. 312/117 X
4,744,175 A * 5/1988 Albright et al. ..... 312/138.1 X
5,860,537 A * 1/1999 Loew .................. 312/138.1 X

* cited by examiner

Primary Examiner—Peter M. Cuomo
Assistant Examiner—Michael J. Fisher
(74) Attorney, Agent, or Firm—Spencer T. Smith

(57) ABSTRACT

A glass container forming machine has a machine base with a vertical front wall which includes a console assembly. This assembly has vertical front and rear box halves which are hingedly connected at the bottom and releasably connected at the top. The rear box is connected to the machine base via vertical hinges so that the console assembly can be pivoted away from the machine base. A console unit having a console screen is hingedly connected at the top proximate the top of the rear box half and the front box half includes vertically extending channels and the bottom of the console unit has followers for following the channels so that as the front box half is pivoted from a closed position whereat the box halves are closed, away from the rear box half to an open position, the console unit will be displaced from an initial position located between the closed front and rear box halves to a final position with the screen exposed and horizontal.

2 Claims, 2 Drawing Sheets

CONSOLE FOR GLASS FORMING MACHINE

BACKGROUND OF THE INVENTION

An operator console should be convenient to the operator but it should be out of the way as much as possible to minimize damage as a result of impact with things moving in the environment of the machine and with the operator.

OBJECT OF THE INVENTION

It is accordingly an object of the present invention to provide a glass-forming machine having a console which is convenient for the operator but is out of the way as much as possible.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE PREFERRED EMBODIMENT

Figure 1:
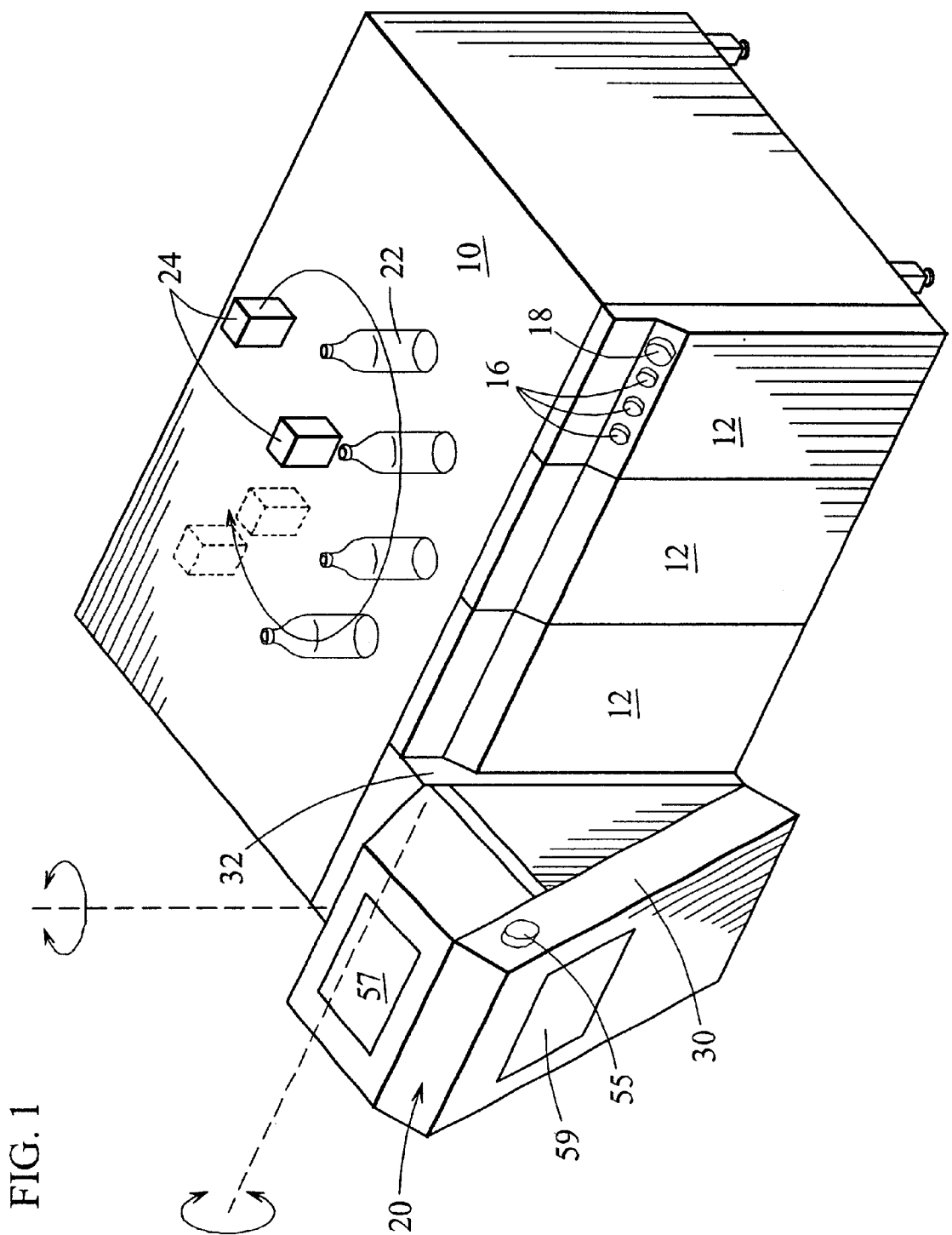
FIG. 1 is a perspective view of a glass-forming machine with the operator console in the use position.

A glass inspection machine has a base 10 which contains some of the electronics (not shown) for the machine. Three access panels 12 close the front right of the base and the right hand most of these access panels includes a number of machine lights 16 and the M.S. button 18. Closing the far left front of the machine base is a console assembly 20. Schematically shown on top of the machine base is a circular flow of bottles 22 passing under a number of inspection devices 24 which could include devices for measuring the I.D. and O.D. of the finish.

Figure 2:
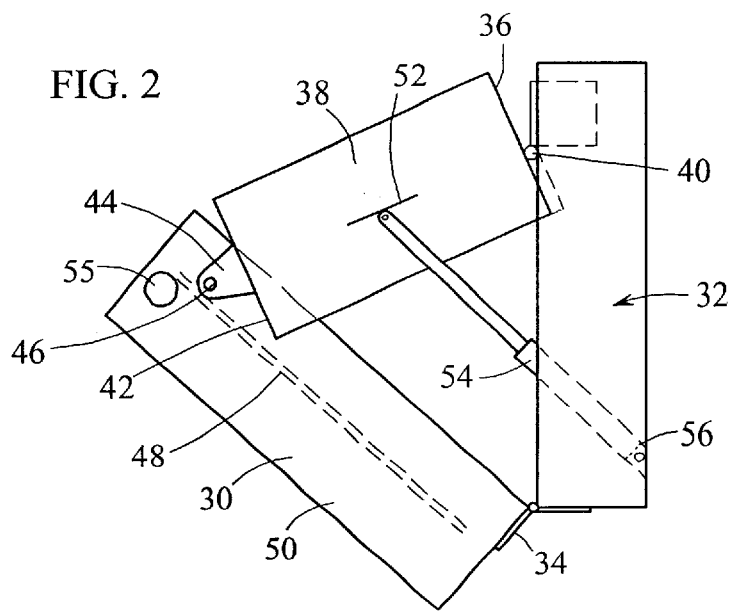
FIG. 2 is a side view of the console shown in FIG. 1.
Figure 3:
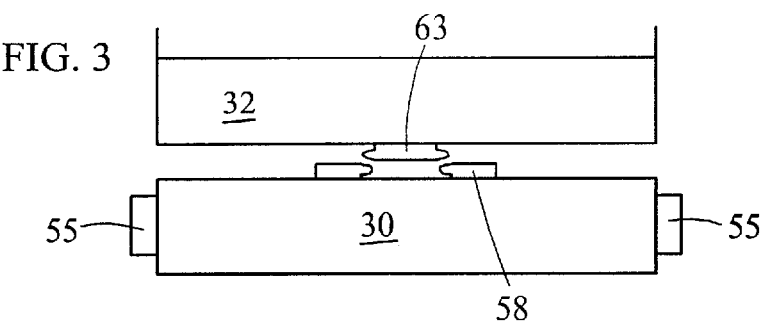
FIG. 3 is a top view of the console slightly separated from the machine frame.
Figure 4:
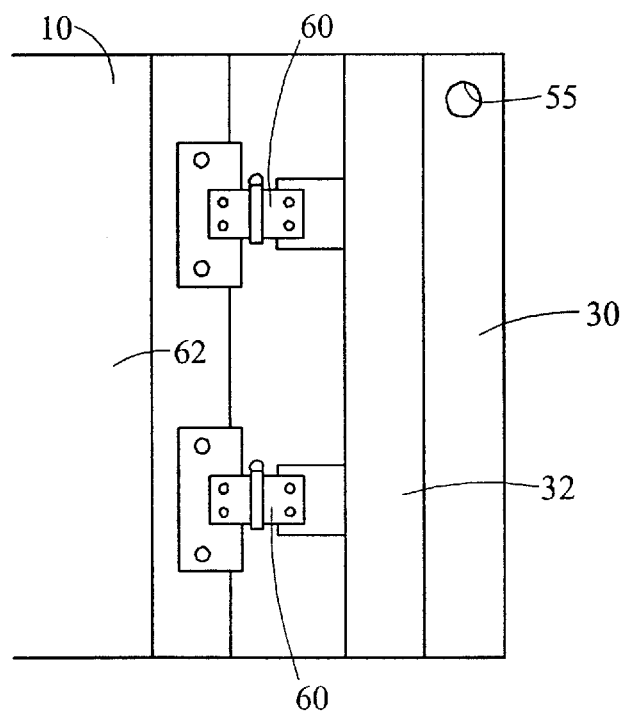
FIG. 4 is a side view, from the other end of the console showing its attachment to the machine frame.

The console assembly has a two part box having front and rear halves 30,32 which are hinged 34 together along the adjacent bottom edges (FIG. 2) and a console unit 38 which is interconnected between the two box halves. As can be seen in FIG. 2, the top 36 (as stowed within the front and rear halves of the console assembly as shown in FIG. 4) of the console unit is hinged 40 to the rear box half proximate the top thereof and the bottom 42 of the console unit has a pair of downwardly extending brackets 44 (one shown) each of which supports a pin 46 captured in a groove 48 defined in the opposed side walls 50 of the front box half. A strut 52 extends between the side walls of the console unit and a biased open pneumatic cylinder 54 extends between the strut and a location proximate the bottom of the rear wall 56 of the rear box half 32.

When an operator grips the opposed knobs 55 and pushes the front box half 30, against the pneumatic cylinder, towards the rear box half 32, the front box half pivots about the bottom hinge 34 and the console unit 38 pivots about the upper pivot 40 as the follower pins 46 proceed down the grooves 48 until the two parts of the box are closed with the console unit located substantially vertically within the closed box. The two halves are detachably connected when a catch 63 on the rear box half is pushed past a pair of detent balls 58 secured to the front box half. When the two box halves are connected, the screen 57 of the console can be viewed through the window 59 in the front box half.

As can be seen from FIG. 4, the rear box half 32 is hinged 60 to a support post 62 of the machine base 10 so the console unit can be pivoted away from the machine base providing access across the entire front of the machine base.

What is claimed is:

1. A glass container inspection machine comprising a machine base including a vertical front wall, said front wall including a console assembly including vertical front and rear box halves hingedly connected at the bottom and releasably connected at the top, vertical hinge means for connecting the rear box to said machine base whereby said console assembly can be pivoted away from the machine base, a console unit having a console screen, said console unit hingedly connected at the top proximate the top of the rear box half, said front box half including vertically extending channel means and the bottom of said console unit having follower means for following said channel means so that as said front box half is pivoted from a closed position whereat the box halves are closed, away from the rear box half to an open position, said console unit will be displaced from an initial position located between the closed front and rear box halves to a final position with the screen exposed and substantially horizontal.

2. A glass container inspection forming machine according to claim 1, wherein said from box half includes a front wall having a window therein so that the screen of said console unit will be seen when said front box half is closed against said second box half.

\* \* \* \* \*